(12) United States Patent
Laue et al.

(10) Patent No.: US 9,272,988 B2
(45) Date of Patent: Mar. 1, 2016

(54) METHOD FOR PRODUCING DIISOCYANATES BY PHOSGENATING DIAMINE SUSPENSIONS

(71) Applicant: Bayer MaterialScience AG, Monheim Am Rhein (DE)

(72) Inventors: Jörg Laue, Olfen (DE); Christian Steffens, Köln (DE); Jens Krause, Leverkusen (DE); Stefan Wershofen, Mönchengladbach (DE); Werner Kilian, Leverkusen (DE); Marc Seekamp, Köln (DE); Matthias Ruhland, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/429,866

(22) PCT Filed: Sep. 18, 2013

(86) PCT No.: PCT/EP2013/069347
§ 371 (c)(1),
(2) Date: Mar. 20, 2015

(87) PCT Pub. No.: WO2014/044699
PCT Pub. Date: Mar. 27, 2014

(65) Prior Publication Data
US 2015/0246873 A1 Sep. 3, 2015

(30) Foreign Application Priority Data

Sep. 24, 2012 (EP) ..................................... 12185575

(51) Int. Cl.
*C07C 263/10* (2006.01)

(52) U.S. Cl.
CPC ........... *C07C 263/10* (2013.01); *C07C 2102/10* (2013.01)

(58) Field of Classification Search
CPC combination set(s) only.
See application file for complete search history.

(56) References Cited

U.S. PATENT DOCUMENTS

| 3,054,565 | A | 9/1962 | Willems |
| 3,188,337 | A | 6/1965 | Gemassmer |
| 3,226,410 | A | 12/1965 | Hettich et al. |
| 3,321,283 | A | 5/1967 | Ewald |
| 3,960,916 | A | * 6/1976 | Fuchs et al. ................... 560/347 |
| 4,289,732 | A | 9/1981 | Bauer et al. |
| 4,419,295 | A | 12/1983 | Hennig et al. |
| 4,851,571 | A | 7/1989 | Sauer et al. |
| 5,117,048 | A | 5/1992 | Zaby et al. |
| 6,225,497 | B1 | 5/2001 | Becker et al. |
| 7,851,648 | B2 | 12/2010 | Sohn et al. |
| 8,362,200 | B2 | 1/2013 | Güntherberg et al. |
| 8,436,204 | B2 | 5/2013 | Knoesche et al. |

FOREIGN PATENT DOCUMENTS

| CA | 832432 A | 1/1970 |
| DE | 949227 C | 9/1956 |
| DE | 1146872 B | 4/1963 |
| DE | 1175666 B | 8/1964 |
| DE | 1792660 A1 | 3/1972 |
| DE | 2404774 A1 | 8/1975 |
| DE | 132340 A1 | 9/1978 |
| DE | 2950216 A1 | 6/1980 |
| DE | 3744001 C1 | 6/1989 |
| DE | 300168 A7 | 5/1992 |
| DE | 196 51 041 A1 | 6/1998 |
| DE | 197 20 959 A1 | 11/1998 |
| DE | 19720959 | * 11/1998 |
| DE | 10260082 A1 | 7/2004 |
| DE | 102005006765 A1 | 8/2006 |
| EP | 0 065 727 A1 | 12/1982 |
| EP | 0 291 819 A2 | 11/1988 |
| EP | 0 928 785 A1 | 7/1999 |
| FR | 69428 E | 11/1958 |
| GB | 901377 A | 7/1962 |
| GB | 1238669 A | 7/1971 |
| GB | 1486344 A | 9/1977 |
| WO | WO-2008/006775 A1 | 1/2008 |
| WO | WO-2009013303 A1 | 1/2009 |

OTHER PUBLICATIONS

International Search Report for PCT/EP2013/069347 mailed Oct. 22, 2013.

* cited by examiner

*Primary Examiner* — Karl J Puttlitz
(74) *Attorney, Agent, or Firm* — Drinker Biddle & Reath LLP

(57) ABSTRACT

The invention relates to a method for producing organic diisocyanates by reacting the corresponding diamines with phosgene in inert solvents. High-melting diamines from the series of 1,5-naphthalenediamine, tetralindiamine, 1,4-phenylenediamine, durenediamine, and o-tolidinediamine are used as diamines. According to the invention, a suspension of the diamines in inert solvents is produced, wherein dynamic mixing units, selected from dispersion disks and rotor-stator systems, are used, and the obtained suspension is phosgenated.

9 Claims, No Drawings

METHOD FOR PRODUCING DIISOCYANATES BY PHOSGENATING DIAMINE SUSPENSIONS

CROSS-REFERENCE TO RELATED APPLICATIONS

This application is a national stage application (under 35 U.S.C. §371) of PCT/EP2013/069347, filed Sep. 18, 2013, which claims benefit of European Application No. 12185575.3, filed Sep. 24, 2012, both of which are incorporated herein by reference in their entirety.

The invention relates to a process for preparing organic diisocyanates by reacting the corresponding diamines with phosgene in inert solvents. Diamines used are high-melting diamines from the group consisting of 1,5-naphthalenediamine, tetralindiamine, 1,4-phenylenediamine, durenediamine and o-tolidinediamine. According to the invention, a suspension of the diamines in inert solvents is produced using dynamic mixing apparatuses selected from among dispersing discs and rotor-stator systems, and the suspension obtained is phosgenated.

Diisocyanates are produced in large quantities and serve mainly as starting materials for the production of polyurethanes. They are usually prepared by reacting the corresponding diamines with phosgene. The continuous preparation of organic isocyanates by reaction of primary organic amines with phosgene has been described many times and is carried out on an industrial scale (see, for example, Ullmanns Encyclopedia of Industrial Chemistry, Wiley-VCH Verlag GmbH & Co KGaA, Weinheim, Online ISBN: 9783527306732, DOI: 10.1002/14356007.a14_611, p. 63 ff (2012)).

In general, the phosgenation is carried out in a two-stage or multistage process. In the first stage of the phosgenation, the amine is reacted with phosgene to form carbamoyl chloride and hydrogen chloride and reacted in a parallel reaction to form amine hydrochloride which, owing to its low solubility in the reaction mixture, generally precipitates as solid. The amine hydrochloride is then reacted with further phosgene to form firstly the carbamoyl chloride. The carbamoyl chlorides are finally converted by elimination of HCl into the corresponding isocyanates. The reaction between amine and phosgene is very fast, exothermic and proceeds even at low temperatures. Further reactions which decrease the yield, e.g. the formation of ureas from isocyanate and amine, proceed parallel thereto. To minimize by-products and solids formation, amine and phosgene therefore have to be mixed quickly, optionally in admixture with an organic solvent, and the reaction has to be carried out with very little backmixing.

Various mixing apparatuses are described in the literature for the purpose of mixing amine and phosgene. The known mixing apparatuses include, in particular, nozzles such as annular slit nozzles (DE-A-1792660), annular hole nozzles (DE-C1-3744001), banking-up nozzles (EP-A-0 065 727), fan jet nozzles (DE-A1-2950216), angled jet nozzles (DD-A7-300.168), three-fluid nozzles (DD-A1-132340), countercurrent mixing chambers (DE-B-1146872), banking-up nozzles (FR-E-69428) and Venturi mixing nozzles (DE-B-1175666). In-line mixers (U.S. Pat. No. 3,321,283), centrifugal or reaction mixing pumps (EP-A-0291 819), tubular reactors (U.S. Pat. No. 3,226,410) or microstructured mixers (EP-A1-0 928 785) are also known. CA-A-832432 describes the use of sound waves for mixing.

Chlorobenzene or o-dichlorobenzene are usually employed as solvent in the processes carried out in industrial practice. These solvents have been found to be useful because, inter alia, they are inert, have good solvent capability and are highly suitable for recovering excess phosgene and separating it from hydrogen chloride formed. However, it is also possible to use other solvents which are inert under the reaction conditions.

In general, it is not necessary to use solvents other than these. However, difficulties occur when the amine to be reacted is sparingly soluble in these solvents.

One possibility for phosgenating sparingly soluble amines is to mix the amines directly in solid form or as a suspension in a solvent with a phosgene solution and react them in this way. This method is based on the reaction of the dissolved amine molecules to form isocyanate bringing further amine molecules into solution and the amine particles gradually dissolving. However, coarse, possibly agglomerated particles which are difficult to phosgenate can be formed in the production of a dispersion by the methods of the prior art. These particles may not react completely in the further course of the reaction, which can lead to not only decreases in yield and selectivity but also to blockages and deposits.

DE-A1-196 51 041 describes a process in which different solvents are used for phosgene solution and amine solution. A disadvantage of this process is an additional outlay for the separation of the solvent mixture before it can be used again.

DE-A1-24 04 774 describes a process for preparing isocyanates in which the amines are converted beforehand into the corresponding amine hydrochlorides in the absence of solvents. The amine hydrochlorides obtained in this way are comminuted to an average particle size of from 1 μm to 100 μm before further phosgenation. The amine hydrochlorides are then reacted in a ratio of at least 2 mol of phosgene per one mol of amine hydrochloride to form the isocyanate. The process described has the disadvantage that the reaction of the amine hydrochloride with phosgene is very slow. This increases the reaction volume required, which affects the costs for the construction of a corresponding plant. In addition, liquefied hydrogen chloride is necessary for producing the amine hydrochlorides, which means an increased outlay for compression and liquefaction of the hydrogen chloride. A particular disadvantage is that very high pressures of from 10 to 60 bar have to be employed. A further great disadvantage is the uneconomical nature of the process since it has to be carried out in two stages. In the first stage, the amine hydrochloride is isolated, and the further reaction to form the diisocyanate occurs in the second stage.

DE-C-949227 describes a cold-hot phosgenation process for the continuous preparation of isocyanates by reaction of amines with phosgene in the liquid phase in the presence of a solvent, in which a solution or slurry of the amine in an inert solvent is combined continuously and without external cooling with liquid phosgene or a solution of phosgene in an inert solvent with intensive stirring in a mixing apparatus in the cold phosgenation and the resulting reaction mixture is then subjected to the hot phosgenation. Turbo mixers and centrifugal pump and mixing devices in general having mechanically moving parts are claimed as mixing device for the mixing of amine and phosgene. The residence time in the mixing device ranges from a few seconds to one minute. Mixing of the feed streams is described. No explicit information is given on the production of the amine solution or amine slurry.

Completion of the reaction to form the isocyanate can be carried out in one or more stages. Examples of possible embodiments are described in DE-A1-10260082.

There is therefore a need for an improved process for preparing high-melting organic diisocyanates from the group consisting of 1,5-naphthalene diisocyanate, 1,4-phenylene diisocyanate, tetralin diisocyanate, o-tolidine diisocyanate and also durene diisocyanate by reaction of the corresponding diamines with phosgene. In particular, minimization of by-product formation and maximization of the yield associated therewith should be ensured.

The present invention therefore provides a process for preparing a diisocyanate selected from the group consisting of naphthalene diisocyanate, phenylene diisocyanate, tetralin diisocyanate, o-tolidine diisocyanate and durene diisocyanate, with naphthalene diisocyanate being preferred, which comprises the following steps:
(i) production of a suspension of the corresponding diamine in an inert solvent, with the diamine being dispersed in the solvent by means of a dynamic mixing apparatus,
(ii) phosgenation of the diamine suspended in the inert solvent to give the respective diisocyanate,
wherein the dynamic mixing apparatus in step (i) is selected from the group consisting of dispersing discs and rotor-stator systems, preferably rotor-stator systems, particularly preferably colloid mills, toothed dispersing machines and three-roll mills. Particular preference is given to toothed dispersing machines as dynamic mixing apparatuses.

In the case of the diamines to be used according to the invention, which isomers are present is unimportant, unless explicitly indicated otherwise. The process of the invention can in principle be applied to any isomer mixtures. However, in the case of naphthalene diisocyanate, the 1,5-isomer (1,5-naphthalene diisocyanate) and in the case of phenylene diisocyanate the 1,4-isomer (1,4-phenylene diisocyanate) are preferably prepared in step i) from the corresponding diamine 1,5-naphthalenediamine or 1,4-phenylenediamine. o-Tolidine diisocyanate has the formula:

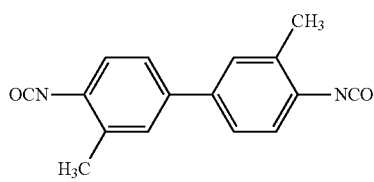

For the purposes of the present invention, dispersing discs are specific disc-shaped stirrers having various shapes and tooth arrangements. High-speed stirrer discs are mainly used for dispersing solid particles in a continuous phase. [See: "http://onlinelibrary.wiley.com/doi/10.1002/cite.200600040/pdf"]. Examples of various dispersing discs are high-performance stirring discs, fine-toothed discs, beater discs, turbine discs. [See: http://www.berndt-scheiben.de/]

For the purposes of the present invention, rotor-stator systems are mixing apparatuses which generate high shear and pushing stresses by means of a combination of rotating and stationary elements. This technique makes it possible to disperse solid (for example fillers) or liquid media uniformly in a liquid matrix. Examples of such rotor-stator systems are colloid mills, toothed dispersing machines and three-roll mills. Three-roll mills are known, for example, from printed ink production as plants for deaerating the printed ink dispersed in the stirred ball mills. Such an apparatus consists of three large cylinders which rotate against one another with different speeds. Three-roll mills are also used in the pharmaceutical formulation sector for deagglomerating and homogenizing the starting material.

Both types of mixing apparatuses make high mixing performances and setting of a defined particle size distribution of the suspended diamine particles possible. The mixing apparatuses mentioned are comprehensively described in *Rotor-Stator and Disc Systems for Emulsification Processes*; Kai Urban, Gerhard Wagner, David Schaffner, Danny Röglin, Joachim Ulrich; *Chemical Engineering & Technology*, 2006, Vol. 29, No. 1, pages 24 to 31, and also in DE-A1-10 2005 006 765, DE-A1-197 20 959 and U.S. Pat. No. 3,054,565.

The invention will be explained in detail below. Here, various embodiments can be combined with one another in any way unless the contrary is not clearly indicated to a person skilled in the art from the context.

In step (i) of the process of the invention, a suspension of the diamine in an inert solvent is produced. Suitable inert solvents are aromatic solvents which may also be halogenated. Examples are toluene, monochlorobenzene, o-, m- or p-dichlorobenzene, trichlorobenzene, chlorotoluenes, chloroxylenes, chloroethylbenzene, chloronaphthalenes, chlorobiphenyls, xylenes, decahydronaphthalene, benzene or mixtures of the above solvents. Further examples of suitable organic solvents are methylene chloride, perchloroethylene, hexane, diethyl isophthalate, tetrahydrofuran (THF), dioxane, trichlorofluoromethane, butyl acetate and dimethylformamide (DMF). Preference is given to using monochlorobenzene or o-dichlorobenzene or a mixture of the two; particular preference is given to using monochlorobenzene.

Production of the diamine suspension is, according to the invention, carried out using dynamic mixing apparatus having a high mixing performance. These are selected from among dispersing discs and rotor-stator systems, preferably rotor-stator systems, particularly preferably colloid mills, toothed dispersing machines and three-roll mills. An example of a toothed dispersing machine is an Ultra-Turrax stirrer. Suitable dynamic mixing apparatuses (rotor-stator systems) can be obtained, for example, from the Ystral company.

It is also possible to assist the formation of the suspension in step (i) by altering the solubility of the diamine in the selected solvent. This can be achieved by cooling, evaporation, precipitation, filtration, etc.

It is also possible to produce the desired suspension in a single-stage or multistage process. Single-stage means that the desired suspension is produced in step (i) by use of a single mixing apparatus; if a plurality of mixing apparatuses are arranged in parallel, such an arrangement likewise comes within the definition of a single-stage process. If a substream or the total stream of the suspension is recirculated either into the single mixing apparatus or into the mixing apparatuses arranged in parallel (recirculation, repeated passage through the single mixing apparatus or the mixing apparatuses arranged in parallel), this mode of operation likewise comes within the definition of a single-stage process. Multistage means that the desired suspension is produced in step (i) by means of a combination of two or more mixing apparatuses arranged in series. The suspension can be divided into substreams according to their particle size by methods known per se from the prior art and the substreams can be recirculated to the dispersing step (step (i)). The desired setting of the particle size distribution is preferably carried out in a single-stage process.

Step (i) of the process of the invention is preferably carried out so that a defined particle size distribution of the suspended diamine is obtained. In the following, the particle size distribution is the volume-weighted size distribution function (measurement of the particle size by means of laser light scattering in accordance with ISO 13320). All parameters mentioned likewise relate to this distribution function or an approximate description and representation thereof by means of a logarithmic normal distribution function. The particle size distribution can in principle also be determined by means of other methods. These include, for example, gravimetric measurement techniques, for example sieve analysis, impactor or cyclone cascade measurement technology. An overview of disperse systems and various measurement methods is given by M. Stiess "Mechanische Verfahrenstechnik 1", Springer-Verlag, Berlin 1995, p. 4ff. However, laser light scattering in accordance with ISO 13320 is the decisive method for the purposes of the present invention.

Preference is given to at least 99% of the amine particles (volume-weighted) in the suspension having a maximum diameter of 1500 µm, preferably 1200 µm, particularly preferably 1000 µm. The average (volume-weighted) particle diameter of the amine particles [D(0.50)] is not more than 140 µm, preferably 130 µm, particularly preferably 125 µm. The particle size distribution usually ranges from very broad to very narrow. The standard deviation σ normalized on the basis of the median of the particle size distribution serves as measure of the width of the distribution. In the case of a very broad distribution, σ is >>1. In the case of a narrow distribution, σ<1 and in the case of an ideally monodisperse distribution the value is σ=0.

The reaction of the amine in the liquid phase brings about a decrease in the concentration of the amine. To reestablish the solution equilibrium, the solid amine dissolves. The dissolution rate is proportional to the solid-liquid phase boundary area available. This in turn is proportional to the particle size distribution. In order to increase the dissolution rate, the particle size should therefore be minimized. The reaction can also take place at the surface of the solid. Here too, the size of the particles should be as small as possible in order to maximize the surface area available for reaction at the solid phase. Furthermore, the maximum size of the precipitating amine hydrochloride particles is in this case limited by the achievable particle diameter. Therefore here too, fine amine particles are preferred to very coarse particles. In contrast to the process described in WO-A1-2008/006775, the lower limit of the particle size is not critical since the isocyanate formed in the reaction dissolves in the solvent and a homogeneous mixture is obtained after complete reaction to isocyanate. In particular, the present invention thus provides a process in which the dispersion of the diamine in the solvent in step (i) is carried out in such a way that the volume-based average particle diameter [D(0.50)] of the suspended diamine obtained in step (i) is not more than 140 µm, preferably not more than 130 µm, particularly preferably not more than 125 µm, and not more than 1.0% by volume of all suspended diamine particles, based on the total volume of all diamine particles, have a volume-based particle diameter of greater than 1500 µm. The particle size distribution achieved depends, inter alia, on the choice of the mixing apparatus, the stirring speed of the mixing apparatus and the number of passes through the mixing apparatus. It is not possible to make generally valid statements here since the particle size distribution achieved depends very greatly on the specific conditions. Suitable conditions can be determined by means of simple production tests.

The production of the diamine suspension can be carried out batchwise or continuously from amine and solvent, e.g. during the introduction into the reactor provided for the phosgenation (step (ii)). Since the diamine suspension usually has a more or less pronounced tendency to undergo sedimentation, the time between production of the diamine suspension and the transfer into the phosgenation reactor for step (ii) should not be too long. Sedimentation can be avoided or at least minimized by suitable apparative measures (e.g. stirring, pumped circulation, etc.). Such a measure is not necessary when, for example, the suspension is produced by mixing of diamine and solvent in the feed line during introduction into the reactor provided for the phosgenation.

The period of time for production of the suspension should likewise not be made too long in order to avoid (partial) decomposition of the amine. The temperature of suspension formation or of the resulting amine suspension is preferably from 0° C. to 150° C., particularly preferably from 0° C. to 100° C. and very particularly preferably from 0° C. to 70° C. The production of the diamine suspension is preferably carried out at an absolute pressure in the range from 1.0 bar to 20 bar, preferably from 1.0 bar to 10 bar, particularly preferably from 1.0 to 5.0 bar. The present invention therefore also provides a process in which the production of the diamine suspension in step (i) is carried out at a temperature of from 0° C. to 150° C. and an absolute pressure of from 1.0 bar to 20 bar.

The phosgene required in step (ii) can either be added after production of the diamine suspension in step (i) or can be present, at least partially, during step (i). In the latter embodiment, the phosgene is preferably initially placed, either partly or completely, in the inert solvent and the diamine is added only then. In this embodiment, phosgenation can occur to a certain extent even during step (i). However, the phosgenation is completed only in step (ii) by increasing the temperature.

If the suspension is produced before mixing with phosgene, the disperse stream containing diamine has to be mixed into the phosgene-containing stream in such a way that the time to attainment of a constant phosgene concentration in the reaction mixture is very short. To ensure this, it is possible to employ all technical methods with which a person skilled in the art is familiar, for example the distributed introduction of phosgene, in cocurrent or in countercurrent, the central, axial rotational introduction of phosgene or the mixing of the feed streams in one or more nozzles, e.g. annular gap nozzles or countercurrent nozzles. Furthermore, it can be advantageous to use dynamic mixers for mixing the diamine suspension with the phosgene. Possible embodiments are described in EP-A2-0 291 819 (see, in particular, column 1, line 41 to column 2, line 44). It can also be advantageous to mix the phosgene-containing solvent into the diamine suspension.

In a further embodiment of mixing, the liquid phosgene or a phosgene solution is initially placed in the reaction space and the diamine suspension is added thereto. This procedure has the advantage that the molar excess of phosgene based on the amine groups is initially very high and attains its target value only at the end of the introduction. Here, the liquid phosgene or the phosgene solution is preferably initially placed in the reaction space at temperatures of from −40° C. to +10° C., particularly preferably of from −20° C. to +0° C. and very particularly preferably at a temperature of from −10 to 0° C.

If the suspension is produced after mixing with phosgene, preference is given to the phosgene required in step (ii) being initially placed at least partly, preferably completely, in the inert solvent in the reaction space at a temperature of from −40° C. to +10° C. and an absolute pressure of from 1.0 bar to 20 bar before addition of the diamine and the phosgenation being completed by increasing the temperature to a value of from 0° C. to 350° C. at an absolute pressure of from 1.0 bar to 20 bar after production of the suspension.

It is advantageous to ensure efficient mixing of the reaction space so that precipitating amine hydrochlorides do not agglomerate to form difficult-to-phosgenate large aggregates. A high space-time yield and an increase in the quality, in particular in respect of the purity, the NCO content, the molecular weight distribution and the by-product spectrum, of the end product can be achieved by efficient mixing.

A suspension of the diamine in the inert solvent having a content of 5.0% by mass to 50% by mass, particularly preferably from 10% by mass to 30% by mass, in each case based on the total mass of the diamine suspension, is preferably produced in step (i) of the process of the invention.

In a further embodiment, the diamine can be used in admixture with further materials which increase the solubility of the amine, the intermediates or the isocyanate. Such materials which are inert under the reaction conditions can be, for example, polar aprotic solvents such as sulfolane, dimethyl sulfoxide (DMSO) or N-methylpyrrolidone (NMP).

The phosgenation in step (ii) of the diamines present as suspension is preferably carried out at an absolute pressure of from 1.0 bar to 20 bar, particularly preferably from 1.0 bar to 10 bar, very particularly preferably from 1.0 bar to 5.0 bar. The reaction temperature is preferably from 0° C. to 350° C., with the temperature preferably being from 50° C. to 50° C., very particularly preferably from 90° C. to 150° C., at the end of the reaction. The present invention therefore also provides a process in which step (ii) is carried out at a temperature of from 0° C. to 350° C. and an absolute pressure of from 1.0 bar to 5.0 bar.

In the reaction in step (ii), phosgene is used in excess. This means that more than one mole of phosgene is used per mole of amine groups. The molar ratio of phosgene to amine groups is accordingly from 1.01:1 to 20:1, preferably from 1.1:1 to 10:1, particularly preferably from 1.1:1 to 5.0:1. Further phosgene or phosgene solution can optionally be introduced into the reaction mixture during the reaction in order to maintain a sufficient phosgene excess or compensate for a loss of phosgene.

The reaction can be carried out continuously or batchwise. Possible reactors are stirred vessels, tube reactors, spray towers or loop reactors. However, it is in principle also possible to use other construction types which are not listed by way of example here. The reaction is preferably carried out batchwise.

The reaction can be continued to complete conversion to the isocyanate within the first reaction stage. However, it can also be advantageous or necessary to carry out a partial conversion, in particular of residual amine hydrochloride, in an after-reactor. The after-reactor can be a conventional reactor construction type having various degrees of backmixing, e.g. stirred vessels, loop reactors or tube reactors. It can also be advantageous to divide the reaction mixture into substreams according to its particle size distribution and feed these separately into one or more after-reactors. Possible construction types for the separation are known apparatuses such as filters, cyclones or gravity separators. The substreams can be treated by means of appropriate mechanical methods for adjusting the particle size, e.g. by milling, before or during the reaction.

The unreacted phosgene is usually, optionally after purification, recirculated and used again for phosgenation.

Compared to conventional liquid-phase phosgenation, the process proposed here using dynamic mixing apparatuses having a high mixing performance for production of the diamine suspension in which preferably at least 99% of the amine particles (volume-weighted) have a maximum diameter of 1500 µm, preferably 1200 µm, particularly preferably 1000 µm, and the average (volume-weighted) particle diameter of the amine particles [D(0.50)] is not more than 140 µm, preferably 130 µm, particularly preferably 125 µm, has the following important advantages:

The reaction mixtures obtained in the phosgenation have a significantly reduced tendency to form by-products. The yield of the isocyanate can be increased as a result. These reduces, inter alia, the outlay for purifying the isocyanate and the specific amount of waste. If the processing capacity of plants for isocyanate production are limited by the waste stream, a higher achievable capacity results from the reduction in the amount of waste. The amine content of the solution or the suspension can be significantly increased by means of the fine dispersion. This reduces the outlay for separating off and working up the solvent.

To separate the diisocyanate from the solvent, it is possible to employ the methods known to those skilled in the art, for example crystallization, sublimation or distillation, optionally with addition of, for example, seed crystals or entrainers. Preference is given to using a method involving crystallization or distillation.

The diisocyanates obtained in step ii) can be passed to all uses with which those skilled in the art are familiar. Particular mention may be made of further processing together with isocyanate-reactive compounds such as polyols to give polyurethanes, optionally via prepolymers as intermediates.

These polyurethanes preferably have apparent densities of from 200 kg/m$^3$ to 1400 kg/m$^3$, particularly preferably from 600 kg/m$^3$ to 1400 kg/m$^3$ and very particularly preferably from 800 kg/m$^3$ to 1400 kg/m$^3$. Very particular preference is given to producing cellular or noncellular casting elastomers, very particularly preferably casting elastomers based on polyester polyol.

The isocyanate component can also contain customary auxiliaries and additives such as rheology improvers (for example ethylene carbonate, propylene carbonate, dibasic esters, citric esters), stabilizers (for example Brönsted and Lewis acids, e.g. hydrochloric acid, phosphoric acid, benzoyl chloride, organomineral acids such as dibutyl phosphate, also adipic acid, malic acid, succinic acid, tartaric acid or citric acid), UV protection agents (for example 2,6-dibutyl-4-methylphenol), hydrolysis inhibitors (for example sterically hindered carbodiimides), emulsifiers and catalysts (for example trialkylamines, diazabicyclooctane, tin dioctoate, dibutyltin dilaurate, N-alkylmorpholine, lead octoate, zinc octoate, tin octoate, calcium octoate, magnesium octoate, the corresponding naphthenates and p-nitrophenoxide and/or phenylmercury neodecanoate) and fillers (for example chalk), optionally dyes which are able to be incorporated into the polyurethane/polyurea to be formed later (which thus have Zerevitinov-active hydrogen atoms) and/or color pigments.

As NCO-reactive compounds, it is possible to use all compounds known to those skilled in the art.

As NCO-reactive compounds, it is possible to use polyether polyols, polyester polyols, polycarbonate polyols and polyetheramines which have an average OH or NH functionality of at least 1.5, and also short-chain polyols and polyamines (chain extenders or crosslinkers), as are adequately known from the prior art. These can be, for example, low molecular weight diols (e.g. 1,2-ethanediol, 1,3- or 1,2-propanediol, 1,4-butanediol), triols (e.g. glycerol, trimethylolpropane) and tetraols (e.g. pentaerythritol), but also relatively high molecular weight polyhydroxy compounds such as polyether polyols, polyester polyols, polycarbonate polyols, polysiloxane polyols, polyamines and polyetherpolyamines and also polybutadiene polyols.

Polyether polyols can be obtained in a manner known per se by alkoxylation of suitable starter molecules in the presence of a base catalyst or using double metal cyanide compounds (DMC compounds). Suitable starter molecules for preparing polyether polyols are, for example, simple, low molecular weight polyols, water, organic polyamines having at least two N—H bonds or any mixture of such starter molecules. Preferred starter molecules for preparing polyether polyols by alkoxylation, in particular by the DMC process, are in particular simple polyols such as ethylene glycol, 1,3-propylene glycol and 1,4-butanediol, 1,6-hexanediol, neopentyl glycol, 2-ethylhexane-1,3-diol, glycerol, trimethylol propane, pentaerythritol and also low molecular weight, hydroxyl-containing esters of such polyols with dicarboxylic acids of the type mentioned by way of example below or low molecular weight ethoxylation or propoxylation products of such simple polyols or any mixtures of such modified or unmodified alcohols. Alkylene oxides suitable for the alkoxylation are, in particular, ethylene oxide and/or propylene oxide, which can be used in any order or else in admixture in the alkoxylation.

Polyester polyols can be prepared in a known manner by polycondensation of low molecular weight polycarboxylic acid derivatives, for example succinic acid, adipic acid, suberic acid, azelaic acid, sebacic acid, dodecanedioic acid, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimer fatty acid, trimer fatty acid, phthalic acid, phthalic anhydride, isophthalic acid, terephthalic acid, citric acid or trimellitic acid, with low molecular weight polyols, for example ethylene glycol, diethylene glycol, neopentyl glycol, hexanediol, butanediol, propylene glycol, glycerol, trimethylolpropane 1,4-hydroxymethylcyclohexane, 2-methyl-1,3-propanediol, 1,2,4-butanetriol, triethylene glycol, tetraethylene glycol, polyethylene glycol, dipropylene glycol, polypropylene glycol, dibutylene glycol and polybutylene glycol, or by ring-opening polymerization of cyclic carboxylic esters such as ε-caprolactone. In addition, hydroxycarboxylic acid derivatives such as lactic acid, cinnamic acid or ω-hydroxycaproic acid can also be polycondensed to form polyester polyols. However, polyester polyols of oleochemical origin can also be used. Such polyester polyols can be prepared, for example, by full ring-opening of epoxidized triglycerides of a fatty acid-containing fat mixture which is at least partially olefinically unsaturated by means of one or more alcohols having from 1 to 12 carbon atoms and subsequent partial esterification of the triglyceride derivatives to form alkylester polyols having from 1 to 12 carbon atoms in the alkyl radical.

The NCO-reactive compound can contain short-chain polyols or polyamines as crosslinker component or chain extender. Typical chain extenders are diethylenetoluenediamine (DETDA), 4,4'-methylenebis(2,6-diethyl)aniline (MDEA), 4,4'-methylenebis(2,6-diisopropyl)aniline (MDIPA), 4,4'-methylenebis(3-chloro-2,6-diethyl)aniline (MCDEA), dimethylthiotoluenediamine (DMTDA, Ethacure® 300), N,N'-di(sec-butyl)aminobiphenylmethane (DB-MDA, Unilink® 4200) or N,N'-di-sec-butyl-p-phenylenediamine (Unilink® 4100), 3,3'-dichloro-4,4'-diaminodiphenylmethane (MBOCA), trimethylene glycol di-p-aminobenzoate (Polacure 740M). Aliphatic amine chain extenders can likewise be used or concomitantly used. 1,3-Propanediol, 1,4-butanediol, 2,3-butanediol, 1,5-pentanediol, 1,6-hexanediol and HQEE (hydroquinone di(3-hydroxyethyl) ether) and also water are suitable. Very particular preference is given to using 1,4-butanediol for noncellular casting elastomers and water for cellular casting elastomers.

An overview of polyurethanes, their properties and uses is given, for example, in Kunststoffhandbuch, volume 7, Polyurethane, 3rd revised edition, volume 193, edited by Prof. Dr. G. W. Becker and Prof. Dr. D. Braun (Carl-Hanser-Verlag, Munich, Vienna).

Preference is given to using NCO-terminated prepolymers having an NCO content of from 2 to 15% by weight, particularly preferably 2-10% by weight. The diisocyanate according to the invention is preferably reacted with polyols having a functionality of from 2 to 3, preferably 2, and an OH number of 28-112 mg KOH/g of substance to form prepolymers. Preference is given to using ester-based polyols. The NCO prepolymers prepared in this way are either further reacted directly or stored as storage-stable prepolymers in, for example, drums until their ultimate use. Preference is given to using 1,5-NDI-based prepolymers. The production of casting elastomers (moldings) is advantageously carried out at an NCO/OH ratio of from 0.7 to 1.30. In the case of cellular elastomers, the amount of the mixture introduced into the mold is usually such that the moldings obtained have the abovementioned density. The starting components are usually introduced at a temperature of from 30 to 110° C. into the mold. The degrees of compaction are in the range from 1.1 to 8, preferably from 2 to 6. Cellular elastomers are advantageously produced using a low-pressure technique or, in particular, the reaction injection molding (RIM) technique in open or preferably closed molds.

The reaction injection molding technique is described, for example, by H. Piechota and H. Röhr in "Integral Schaumstoffe", Carl Hanser-Verlag, Munich, Vienna 1975; D. J. Prepelka and J. L. Wharton in Journal of Cellular Plastics, March/April 1975, pages 87 to 98 and U. Knipp in Journal of Cellular Plastics, March/April 1973, pages 76-84.

Additives such as castor oil or carbodiimides (e.g. Stabaxols from Rheinchemie as hydrolysis inhibitors; 2,2',6,6'-tetraisopropyldiphenylcarbodiimide is a known representative) can be added both to the polyol and to the prepolymer. Water, emulsifiers, catalysts and/or auxiliaries and/or additives together with the polyol customarily form the polyol component.

To improve removal from the mold, it is usual to provide the molds with external release agents, for example compounds based on wax or silicone or aqueous soap solutions. The demolded moldings are usually kept at temperatures of from 70 to 120° C. for from 1 to 48 hours.

Emulsifiers used are, for example, sulfonated fatty acids and also further generally known emulsifiers, e.g. polyglycol esters of fatty acids, alkyl aryl polyglycol ethers, alkoxylates of fatty acids, preferably polyethylene glycol esters, polypropylene glycol esters, polyethylene-polypropylene glycol esters, ethoxylates and/or propoxylates of linoleic acid, linolenic acid, oleic acid, arachidonic acid, particularly preferably oleic acid ethoxylates. As an alternative, it is also possible to use polysiloxanes. Salts of fatty acids with amines, e.g. diethylamine oleate, diethanolamine stearate, diethanolamine ricinoleate, salts of sulfonic acids, e.g. alkali metal or ammonium salts of dodecylbenzene sulfonic or dinaphthylmethanedisulfonic acid, are likewise preferred.

The sulfonated fatty acids may preferably be used as aqueous solutions, for example as 50% strength solution. Typical known products are Zusatzmittel SV and SM from Rheinchemie and also Zusatzmittel WM from Rheinchemie as non-aqueous emulsifier.

The process for producing the cellular PUR casting elastomers is carried out in the presence of water. The water acts both as crosslinker with formation of urea groups and also, owing to the reaction with isocyanate groups to form carbon dioxide, as blowing agent. The amounts of water which can advantageously be used are from 0.01 to 5% by weight, preferably from 0.3 to 3.0% by weight, based on the weight of the component (b). The water can be used completely or partly in the form of the aqueous solutions of the sulfonated fatty acids.

The catalysts can be added individually or in admixture with one another. They are preferably metal-organic compounds such as tin(II) salts of organic carboxylic acids, e.g. tin(II) dioctoate, tin(II) dilaurate, dibutyltin diacetate and dibutyltin dilaurate, and tertiary amines such as tetramethylethylenediamine, N-methylmorpholine, diethylbenzylamine, triethylamine, dimethylcyclohexylamine, diazabicyclooctane, N,N'-dimethylpiperazine, N-methyl-N'-(4-N-dimethylamino)butylpiperazine, N,N,N',N'',N''-pentamethyldiethylenetriamine or the like. Further possible catalysts are: amidines such as 2,3-dimethyl-3,4,5,6-tetrahydropyrimidine, tris(dialkylaminoalkyl)-s-hexahydrotriazines, in particular tris(N,N-dimethylaminopropyl)-s-hexahydrotriazine, tetraalkylammonium hydroxides such as tetramethylammonium hydroxide, alkali metal hydroxides such as sodium hydroxide and alkali metal alkoxides such as sodium methoxide and potassium isopropoxide and also alkali metal salts of long-chain fatty acids having from 10 to 20 carbon atoms and optionally lateral OH groups. Depending on the reactivity to be set, the catalysts (b4) are employed in amounts of from 0.001 to 0.5% by weight, based on the component (a).

Such cellular PUR casting elastomers, also referred to as moldings, are used as damping elements in vehicle construction, for example in automobile construction, e.g. as supplementary springs, buffer elements, transverse arm bearings, rear axle subframe bearings, stabilizer bearings, longitudinal strut bearings, MacPherson strut bearings, shock absorber bearings, bearings for wishbones and as emergency wheel which is located on the wheel rim and, for example, in the case of tire damage allows the vehicle to run on the cellular elastomer and remain controllable. The noncellular casting elastomers can also be used as coating for rollers, wheels and rolls, doctor blades, screens or hydrocyclones.

EXAMPLES

Example 1 (Comparative Example)

Production of a Suspension of 1,5-Napthalene Diamin (1,5-NDA) Using a Blade Stirrer A suspension was produced under a nitrogen atmosphere from 50 g of pulverulent, solid 1,5-NDA and 150 g of dry chlorobenzene (MCB) by stirring for 10 minutes with a blade stirrer at 400 revolutions per minute. The resulting particle size distribution is documented in table 1 (measurement of the particle size by means of laser light scattering in accordance with ISO 13320).

Example 2 (According to the Invention)

Production of a Suspension of 1,5-NDA Using an Ultra-TURRAX

A suspension was produced under a nitrogen atmosphere from 50 g of pulverulent, solid 1,5-NDA and 150 g of dry chlorobenzene (MCB) by stirring for 1 minute with an Ultra-TURRAX (a rotor-stator system, namely a toothed dispersing machine) at 10 000 revolutions per minute. The resulting particle size distribution is documented in table 1 (measurement of the particle size by means of laser light scattering in accordance with ISO 13320).

TABLE 1

Particle size distribution in examples 1 and 2

| Distribution | Example 1: blade stirrer [µm] | Example 2: Ultra-TURRAX [µm] | Reduction in the particle size in example 2 compared to example 1 by |
|---|---|---|---|
| D (0.06) | 40.7 | 30.9 | 24% |
| D (0.10) | 52.8 | 40.4 | 23% |
| D (0.15) | 64.9 | 50.4 | 22% |
| D (0.20) | 75.9 | 59.7 | 21% |
| D (0.30) | 97.1 | 78.1 | 20% |
| D (0.50) | 144.9 | 121.6 | 16% |
| D (0.85) | 321.0 | 291.9 | 9% |
| D (0.90) | 383.5 | 352.3 | 8% |

The reduction in the average particle size is thus from about 8 to 24%, depending on the particle size.

Example 3 (Comparative Example)

Phosgenation of a Suspension of 1,5-NDA which was Produced Using a Blade Stirrer In a phosgenation apparatus, a solution of 120 g of phosgene in 300 g of chlorobenzene was produced at 0° C. by condensing phosgene from a pressurized gas bottle into chlorobenzene. While stirring, a suspension produced as per example 1 and containing 50 g of technical-grade 1,5-diaminonaphthalene (purity 99.2% according to GC) in 150 g of chlorobenzene was added all at once to the phosgene solution. The mixture was subsequently heated to reflux over a period of 120 minutes while continuously passing gaseous phosgene from the pressurized gas bottle (about 5-10 l/h) through the reaction mixture and the mixture was kept under reflux for 10 hours. Excess phosgene was then removed by distilling off phosgene and part of the chlorobenzene in a water pump vacuum. The mixture was then fractionally distilled under reduced pressure. The yield of 1,5-naphthalene diisocyanate (1,5-NDI) was 75.6% of theory.

Example 4 (According to the Invention)

Phosgenation of a Suspension of 1,5-NDA which was Produced Using an Ultra-TURRAX In a phosgenation apparatus, a solution of 120 g of phosgene in 300 g of chlorobenzene was produced at 0° C. by condensing phosgene from a pressurized gas bottle into chlorobenzene. While stirring, a suspension produced as per example 2 and containing 50 g of technical-grade 1,5-diaminonaphthalene (purity 99.2% according to GC) in 150 g of chlorobenzene was added all at once to the phosgene solution. The mixture was subsequently heated to reflux over a period of 120 minutes while continuously passing gaseous phosgene from the pressurized gas bottle (about 5-10 l/h) through the reaction mixture and the mixture was kept under reflux for 10 hours. Excess phosgene was then removed by distilling off phosgene and part of the chlorobenzene in a water pump vacuum. The mixture was then fractionally distilled under reduced pressure. The yield of 1,5-NDI was 82.8% of theory.

Comparison of examples 3 and 4 clearly shows that the use of a highly effective mixing apparatus for producing the 1,5-NDA suspension in chlorobenzene leads to a significant improvement in the yield of 1,5-NDI.

The invention claimed is:
1. A process for preparing a diisocyanate selected from the group consisting of naphthalene diisocyanate, phenylene diisocyanate, tetralin diisocyanate, o-tolidine diisocyanate and durene diisocyanate, which comprises the following steps:

(i) producing a suspension of the corresponding diamine in an inert solvent, with the diamine being dispersed in the solvent by means of a dynamic mixing apparatus, (ii) contacting the diamine suspended in the inert solvent with phosgene to give the respective diisocyanate, wherein the dynamic mixing apparatus in step (i) is selected from the group consisting of dispersing discs and rotor-stator systems.

2. The process as claimed in claim 1, wherein the dynamic mixing apparatus in step (i) is a rotor-stator system.

3. The process as claimed in claim 2, wherein the rotor-stator system is selected from the group consisting of colloid mills, toothed dispersing machines and three-roll mills.

4. The process as claimed in claim 3, wherein the rotor-stator system is a toothed dispersing machine.

5. The process as claimed in claim 1, wherein the dispersing of the diamine in the solvent in step (i) is carried out in such a way that the volume-based average particle diameter D(0.50) of the suspended diamine obtained in step (i) is not more than 140 μm and not more than 1.0% by volume of all suspended diamine particles, based on the total volume of all diamine particles, have a volume-based particle diameter of greater than 1500 μm.

6. The process as claimed in claim 1, wherein step (i) is carried out at a temperature of from 0° C. to 150° C. and an absolute pressure of from 1.0 bar to 20 bar.

7. The process as claimed in claim 1, wherein step (ii) is carried out at a temperature of from 0° C. to 350° C. and an absolute pressure of from 1.0 bar to 5.0 bar.

8. The process as claimed in claim 1, wherein the phosgene required in step (ii) is at least partly placed initially in the inert solvent at a temperature of from −40° C. to +10° C. and an absolute pressure of from 1.0 bar to 20 bar before addition of the diamine and the phosgenation is completed by increasing the temperature to a value in the range from 0° C. to 350° C. at an absolute pressure of from 1.0 bar to 20 bar after production of the suspension.

9. The process as claimed in claim 1, wherein the diisocyanate is naphthalene diisocyanate.

* * * * *